(12) United States Patent
Jethmalani et al.

(10) Patent No.: US 7,134,755 B2
(45) Date of Patent: Nov. 14, 2006

(54) CUSTOMIZED LENSES

(75) Inventors: Jagdish M. Jethmalani, San Diego, CA (US); Christian A. Sandstedt, Pasadena, CA (US); Robert H. Grubbs, South Pasadena, CA (US)

(73) Assignee: Calhoun Vision, Inc., Pasadena, CA (US)

( * ) Notice: Subject to any disclaimer, the term of this patent is extended or adjusted under 35 U.S.C. 154(b) by 0 days.

(21) Appl. No.: 11/093,899

(22) Filed: Mar. 30, 2005

(65) Prior Publication Data

US 2005/0195361 A1     Sep. 8, 2005

Related U.S. Application Data

(63) Continuation of application No. 10/212,454, filed on Aug. 5, 2002, now abandoned, and a continuation-in-part of application No. 10/175,552, filed on Jun. 18, 2002, which is a continuation of application No. 09/416,044, filed on Oct. 8, 1999, now Pat. No. 6,450,642.

(60) Provisional application No. 60/140,298, filed on Jun. 17, 1999, provisional application No. 60/115,617, filed on Jan. 12, 1999, provisional application No. 60/344,248, filed on Dec. 28, 2001, provisional application No. 60/132,871, filed on May 5, 1999.

(51) Int. Cl.
  *A61B 3/10*     (2006.01)
(52) U.S. Cl. ...................................................... 351/213
(58) Field of Classification Search ................. 351/212, 351/213, 216–219; 451/5
  See application file for complete search history.

(56) References Cited

U.S. PATENT DOCUMENTS

| | | | |
|---|---|---|---|
| 6,086,204 A * | 7/2000 | Magnante | 351/212 |
| 6,450,642 B1 * | 9/2002 | Jethmalani et al. | 351/219 |
| 6,682,195 B1 | 1/2004 | Dreher | |
| 6,712,466 B1 | 3/2004 | Dreher | |
| 6,813,082 B1 | 11/2004 | Bruns | |
| 6,890,241 B1 * | 5/2005 | Kozakai et al. | 451/5 |

* cited by examiner

*Primary Examiner*—George Manuel
(74) *Attorney, Agent, or Firm*—Fulbright & Jaworski LLP

(57) ABSTRACT

The invention relates to a method of customizing lenses using an external stimulus such as light. Fine-tuning of the lens to match the precise optical requirements using the same lens is also possible. The lenses are self-contained and do not require the addition or removal of significant portions of the lens to achieve customization.

16 Claims, No Drawings

CUSTOMIZED LENSES

CROSS-REFERENCE TO RELATED APPLICATIONS

This Application is a Continuation of application Ser. No. 10/212,454 filed on Aug. 5, 2002, now abandoned which application claims priority to provisional application 60/344,248, filed on Dec. 28, 2001. This application is also a continuation-in-part of application Ser. No. 10/175,552, filed on Jun. 18, 2002, which is a continuation of U.S. patent application Ser. No. 09/416,044 filed Oct. 8, 1999, now U.S. Pat. No. 6,450,642, which claims priority to provisional application 60/140,298 filed Jun. 17, 1999; 60/132,871, filed May 5, 1999 and 60/115,617 filed Jan. 12, 1999.

STATEMENT REGARDING FEDERALLY SPONSORED RESEARCH OR DEVELOPMENT

Not applicable.

REFERENCE TO A COMPACT DISK APPENDIX

Not applicable.

BRIEF SUMMARY OF THE INVENTION

The present invention is directed to customized lenses and a method for making them. In one embodiment, lenses are provided whose optical properties can be customized through the use of external stimuli such as light or other radiation.

BACKGROUND OF THE INVENTION

The most common method for correcting vision is through the use of corrective lenses, e.g., spectacles, contact lenses, and intraocular lenses. In the case of each of these lenses, the lenses are prefabricated with a specific set of optical properties, mostly optical power.

In some cases, the lenses are capable of some post-fabrication modification (e.g., grinding of lenses). In many cases, the lenses must be prefabricated to a specific power or diopter. In still other instances, the desired optical properties must be estimated and the lenses specifically fabricated. The latter process can be time-consuming and inexact.

The typical solution to this problem has been the maintenance of an inventory of lenses with a wide assortment of optical powers. For example, an optometrist often maintains a large inventory of contact lenses having different diopter values so that prescriptions can be quickly filled. When a lens is out of stock or when a patient requires a custom lens, special orders must be made, causing delays in dispensing the lens.

Thus, there exists a need for lenses which can be readily customized to fit the patient's needs. In this manner, precise correction of the patient's vision can be performed without significant delay or expense.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

SUMMARY OF THE INVENTION

Customizable lenses are provided whose optical properties can be adjusted post-manufacture without the addition or removal of material from the lens. The lenses are self-contained units having dispersed therein a modifying composition ("MC") which, when exposed to an external stimulus, changes the optical properties of the lens.

As used herein, the term "self-contained" means that the lenses are self supporting and contain all the elements necessary to affect the change in optical properties without the addition or removal of modifying compositions. For example, in the preferred embodiment, the lenses comprise a fully or partially cross-linked polymer matrix having MCs dispersed throughout the matrix. Only the exposure of a portion of the MC to an external stimulus followed by the polymerization of the MC within the matrix in the said portion is required to affect the changes in optical properties. No modifying composition is added or removed from the lens to induce the change in properties.

A method for preparing customized lenses is also provided. In the method, the correction requirements of the patient is determined. A lens containing a modifying composition is selected. The lens is then exposed to an external stimulus in a manner that the optical properties of the lens are changed so as to provide the desired vision correction. The lenses are then dispensed to the patient. Adjustments can be made without adding or removing modifying composition.

DETAILED DESCRIPTION OF THE INVENTION

Corrective lenses are provided which can be customized, post-manufacture, to suit the specific needs of the user. The optical properties of the lenses can be modified without the addition or removal of materials from the lens.

The lenses contain a MC dispersed throughout the lens. The MC is capable of stimulus-induced polymerization and can freely diffuse or migrate within the lens.

In one embodiment, the lens is formed from a first polymer matrix which has the MC dispersed throughout. The first polymer matrix gives the lens its basic shape as well as its physical properties, such as hardness, clarity, flexibility and the like.

The nature of the first polymer matrix and the MC will vary depending upon the end use contemplated for the optical element. However, as a general rule, the first polymer matrix and the MC are selected such that the components that comprise the MC are capable of diffusion within the first polymer matrix. Put another way, a loose first polymer matrix will tend to be paired with larger MC components and a tight first polymer matrix will tend to be paired with smaller MC components. While the FPM generally comprises a crosslinked matrix, the FPM need not be fully crosslinked, but may be partially crosslinked. The only requirement is that the FPM be self supportive and allow the diffusion of the MC within the FPM and allow the crosslinking of MC upon exposure to the appropriate stimulus.

Upon exposure to an appropriate energy (e.g., heat or light), the MC typically forms a second polymer matrix in the exposed region of the optical element. The presence of the second polymer matrix changes the material characteristics of this portion of the optical element to modulate its refraction capabilities. In general, the formation of the second polymer matrix typically increases the refractive index of the affected portion of the optical element. After exposure, the MC in the unexposed region will migrate into the exposed region over time. The amount of MC migration into the exposed region is time dependent and may be precisely controlled. If enough time is permitted, the MC components will re-equilibrate and redistribute throughout optical element (i.e., the first polymer matrix, including the exposed region). When the region is re-exposed to the energy source, the MC that has since migrated into the region (which may be less than if the MC were allowed to re-equilibrate) polymerizes to further increase the formation of the second polymer matrix. This process (exposure followed by an appropriate time interval to allow for diffusion) may be repeated until the exposed region of the optical element has reached the desired property (e.g., power, refractive index, or shape).

The first polymer matrix is a covalently or physically linked structure that functions as an optical element and is formed from a first polymer matrix composition ("FPMC"). In general, the first polymer matrix composition comprises one or more monomers that upon polymerization will form the first polymer matrix. The first polymer matrix composition optionally may include any number of formulation auxiliaries that modulate the polymerization reaction or improve any property of the optical element. Illustrative examples of suitable FPMC monomers include acrylics, methacrylates, phosphazenes, siloxanes, vinyls, homopolymers and copolymers thereof. As used herein, a "monomer" refers to any unit (which may itself either be a homopolymer or copolymer) which may be linked together to form a polymer containing repeating units of the same. If the FPMC monomer is a copolymer, it may be comprised of the same type of monomers (e.g., two different siloxanes) or it may be comprised of different types of monomers (e.g., a siloxane and an acrylic).

In one embodiment, the one or more monomers that form the first polymer matrix are polymerized and cross-linked in the presence of the MC. In another embodiment, polymeric starting material that forms the first polymer matrix is cross-linked in the presence of the MC. Under either scenario, the MC components must be compatible with and not appreciably interfere with the formation of the first polymer matrix. Similarly, the formation of the second polymer matrix should also be compatible with the existing first polymer matrix. Put another way, the first polymer matrix and the second polymer matrix should not phase separate and light transmission by the optical element should be unaffected.

As described previously, the MC may be a single component or multiple components so long as: (i) it is compatible with the formation of the first polymer matrix; (ii) it remains capable of stimulus-induced polymerization after the formation of the first polymer matrix: and (iii) it is freely diffusable within the first polymer matrix. In preferred embodiments, the stimulus-induced polymerization is photoinduced polymerization.

The inventive lenses comprises a first polymer matrix and a MC dispersed therein. The first polymer matrix and the MC are as described above with the additional requirement that the resulting lens be biocompatible.

Illustrative examples of a suitable first polymer matrix include: polyacrylates such as polyalkyl acrylates and polyhydroxyalkyl acrylates; polymethacrylates such as polymethyl methacrylate ("PMMA"), a polyhydroxyethyl methacrylate ("PHEMA"), and polyhydroxypropyl methacrylate ("HPMA"); polyvinyls such as polystyrene and polyvinylpyrrolidone ("NVP"); polyvinyl alcohols with polymerizable end groups such as methacrylate side groups; polysiloxanes such as polydimethylsiloxane; polyphosphazenes, and copolymers thereof. U.S. Pat. No. 4,260,725 and patents and references cited therein (which are all incorporated herein by reference) provide more specific examples of suitable polymers that may be used to form the first polymer matrix.

In embodiments where flexibility is desired (e.g., contact lenses), the first polymer matrix generally possesses a relatively low glass transition temperature ("$T_g$") such that the resulting lens tends to exhibit fluid-like and/or elastomeric behavior, and is typically formed by cross-linking one or more polymeric starting materials wherein each polymeric starting material includes at least one cross-linkable group. In other embodiments, flexibility is less important (e.g., spectacle lenses). In this case, the monomers are such that the finished lens has a $T_g$ of >25° C. In another embodiment, the FPM and MC are dissolved in a suitable medium. The solution is then exposed to an external stimulus causing the crosslinking of the FPM and some of the MC to form a self supporting structure being MC dispersed therein. The optical properties of the lens are then modified by the re-exposing the lens to the external stimulus. This causes further polymerization of the full MC and inducing changes in the lens with manner described above. Alternatively, if the MC has already been crosslinked, if there are additional reactive groups present, further crosslinking can occur inducing additional changes in optical properties.

Illustrative examples of suitable cross-linkable groups include but are not limited to hydride, acrylate, methacrylate, acetoxy, alkoxy, amino, anhydride, aryloxy, carboxy, enoxy, epoxy, halide, isocyano, olefinic, and oxine. In one preferred embodiments, each polymeric starting material includes terminal monomers (also referred to as endcaps) that are either the same or different from the one or more monomers that comprise the polymeric starting materials but include at least one cross-linkable group. In other words, the terminal monomers begin and end the polymeric starting material and include at least one cross-linkable group as part of their structure. In second preferred embodiments, each polymeric starting material has crosslinkable groups present either at the terminal ends or side groups or both which can crosslink to form the network (e.g. CIBA's patents—crosslinking occurs via the reactive side groups along the polymer backbone. In one preferred embodiment, the mechanism for cross-linking the polymeric starting material preferably is different than the mechanism for the stimulus-induced polymerization of the components that comprise the MC. For example, if the MC is polymerized by photoinduced polymerization, then it is preferred that the polymeric starting materials have cross-linkable groups that are polymerized by any mechanism other than photoinduced polymerization.

In an alternative embodiment, the polymerization mechanism for the MC and the starting materials for the first polymer matrix can be the same, but the rates of polymerization must be different such that the first polymer matrix is substantially complete before significant amounts of MC have been polymerized. For example, where photopolymerization is used to form the first polymer matrix and to polymerize the MC, the starting material for the first polymer matrix may contain reactive methacrylate groups as the polymerizable moiety whereas the MC may contain reactive acrylate groups. These groups photopolymerize at significantly different rates allowing the formation of the first polymer matrix before significant amounts of the MC have polymerized.

An especially preferred class of polymeric starting materials for the formation of the first polymer matrix is polysiloxanes (also known as "silicones") endcapped with a terminal monomer which includes a cross-linkable group selected from the group consisting of acetoxy, amino, alkoxy, halide, hydroxy, and mercapto. Because silicone IOLS tend to be flexible and foldable, generally smaller incisions may be used during the IOL implantation procedure. An example of an especially preferred polymeric starting material is bis(diacetoxymethylsilyl)-polydimethysiloxane (which is polydimethylsiloxane that is endcapped with a diacetoxymethylsilyl terminal monomer).

Another class of materials that may be useful in forming the lenses of the invention are acetal derivatives of polyvinyl alcohols PVAs having crosslinkable end groups such as methacrylate groups along the backbone of the PVA. Illustrative examples of such materials are described in U.S. Pat. No. 5,508,317, the teachings of which are incorporated by reference. The derivatized PVA should have a molecular weight of at least 10,000.

Still another class of materials that may be useful in the practice of the invention are polyhydroxymethacrylates (poly(HEMA)) having polymerizable groups such as those described in U.S. Pat. Nos. 4,495,313 and 4,680,336, the teachings of which are hereby incorporated by reference. The (poly(HEMA))s should have a molecular weight of at least 10,000.

The MC that is used in fabricating IOLs is as described above except that it has the additional requirement of biocompatibility. The MC is capable of stimulus-induced polymerization and may be a single component or multiple components so long as: (i) it is compatible with the formation of the first polymer matrix; (ii) it remains dispersed in the FPM and is capable of stimulus-induced polymerization after the formation of the first polymer matrix; and (iii) it is freely diffusable within the first polymer matrix. In general, the same type of monomers that are used to form the first polymer matrix may be used as components of the MC. However, because of the requirement that the MC monomers must be diffusable within the first polymer matrix, the MC monomers generally tend to be smaller (i.e., have lower molecular weights) than the monomers which form the first polymer matrix. In addition to the one or more monomers, the MC may include other components such as initiators and sensitizers that facilitate the formation of the second polymer matrix.

Because of the preference for flexible and foldable IOLs and flexible contact lenses, an especially preferred class of MC monomers is polysiloxanes endcapped with a terminal siloxane moiety that includes a photopolymerizable group. An illustrative representation of such a monomer is:

wherein Y is a siloxane which may be a monomer, a homopolymer or a copolymer formed from any number of siloxane units, and X and $X^1$ may be the same or different and each contain a moiety that includes a photopolymerizable group. Illustrative examples of Y include:

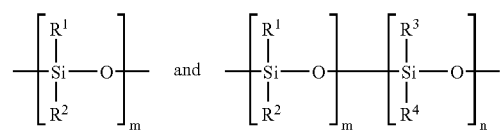

wherein: m and n are independently each an integer and $R^1$, $R^2$, $R^3$, and $R^4$, are independently each hydrogen, alkyl (primary, secondary, tertiary, cyclo), aryl, or heteroaryl. In preferred embodiments, $R^1$, $R^2$, $R^3$, and $R^4$, is a $C_1$–$C_{10}$ alkyl or phenyl. Because MC monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, $R^3$ are the same and are methyl, ethyl or propyl and $R^4$ is phenyl.

Illustrative examples of X and $X^1$ (or $X^1$ and X depending on how the MC polymer is depicted) are

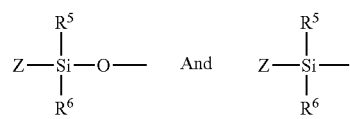

respectively wherein:

$R^5$ and $R^6$ are independently each hydrogen, alkyl, aryl, or heteroaryl; and Z is a photopolymerizable group.

In preferred embodiments $R^1$ and $R^6$ are independently each a $C_1$ and $C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ is methyl, ethyl, or propyl and Z is a photopolymerizable group that includes an acrylate or methacrylate moiety.

In addition to the silicone-based MCs described above, acrylate-based MC can also be used in the practice of the invention. The acrylate-based macromers of the invention have the general structure

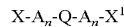

or

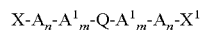

wherein Q is an acrylate moiety capable of acting as an initiator for Atom Transfer Radical Polymerization ("ATRP"), A and $A^1$ have the general structure:

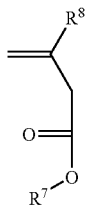

wherein $R^7$ is selected from the group comprising alkyls, halogenated alkyls, aryls and halogenated aryls, and $R^8$ equals H, $CH_3$, alkyl, and fluoroalkyl, and X and $X^1$ are groups containing photopolymerizable moieties and m and n are integers.

In one embodiment the acrylate based MC has the formula

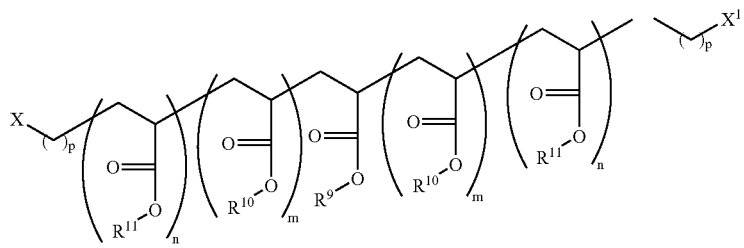

wherein $R^9$ is selected from the group comprising alkyls and halogenated alkyls $R^{10}$ and $R^{11}$ are different and are selected from the group consisting of alkyls, halogenated alkyls, aryls and halogenated aryls, x and $x^1$ are as defined above and is either zero or an integer.

In especially preferred embodiments, an MC monomer is of the following formula:

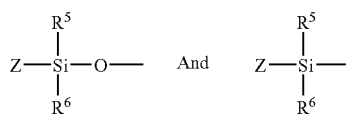

wherein x and $x^1$ are the same and $R^1$, $R^2$, $R^3$, and $R^4$ are as defined previously. Illustrative examples of such MC monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group. Although any suitable method may be used, a ring-opening reaction of one of more cyclic siloxanes in the presence of triflic acid has been found to be a particularly efficient method of making one class of inventive MC monomers. Briefly, the method comprises contacting a cyclic siloxane with a compound of the formula:

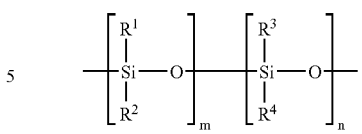

in the presence of triflic acid wherein $R^5$, $R^6$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethyl-siloxane methyl-phenylsiloxane copolymer that is endcapped with a methacryloxylpropyl-dimethylsilane group, an especially preferred MC monomer.

In another embodiment, where the first polymer matrix is formed from derivatized PVAs of from (poly(HEMA)s with reactive groups, the MC may be formed from the same compositions, but with significantly lower molecular weights (i.e. ~1,000) and with reactive groups which polymerize via a different mechanism, or at a substantially different rate. In one embodiment, the first polymer matrix is formed by the photopolymerization of an acetal derivatized PVA having reactive methacrylate side groups. The derivaized PVA has a molecular weight of about 10,000. In this case, the MC may comprise a similar derivatized PVA with a lower molecular weight (~1000) and having reactive acrylate side groups. Upon exposure to photoradiation, the higher molecular weight derivatized PVA will polymerize faster than the MC forming the polymer matrix before significant amounts of the MC have been polymerized. This creates a polymer matrix with free MC dispersed therein. The free MC is then available for further polymerization as part of the customization process. Similar results may be achieved using high and low molecular weight (poly(HEMA)s with different polymerizable side groups.

As discussed above, the stimulus-induced polymerization requires the presence of an initiator. The initiator is such that upon exposure to a specific stimuli, it induces or initiates the polymerization of the MC. In the preferred embodiment, the initiator is a photoinitiator. The photoinitiator may also be associated with a sensitizer. Examples of photoinitiators suitable for use in the practice of the invention are acetophenones (e.g., substituted haloaceto phenones and diethoxyacetophenone); 2,4-dichloromethyl-1,3,5-triazines; benzoin methyl ether; and O-benzoyl oximino ketone.

Suitable sensitizers include p-(dialkylamino aldehyde); n-alkylindolylidene; and bis [p-(dialkyl amino) benzylidene] ketone.

In practice of the invention, lenses are prefabricated in the manner described above. These lenses are then modified based on the patient's specific needs in the following manner.

First, the patient is examined to determine the individual's specific optical needs. This examination is the same as routinely conducted by ophthalmologists and optometrists. It may involve autorefraction, wavefront based aberrometric analysis, surface topography, and the like.

Based on the results of the examination, a prescription is developed, specifying the desired properties for the lenses. This can include correction for myopia, astigmatism and the like. Once these correction values have been determined, an unmodified lens is then exposed to an external stimulus in a pattern and at sufficient intensity to induce the desired changes in the lenses. Once the desired properties have been achieved, the lenses are dispersed to the patient.

The lens is modified by exposing the lens to an external stimulus in a pattern to modify the optical properties of the lens to correct the vision of the patient. This is accomplished by either altering the refraction index of the lens or by changes in the shape of the lens, or both. In the preferred embodiment, the change in refraction is caused by polymerization of MC in at least a portion of the lens coupled with migration of unpolymerized MC within the lens to reestablish a uniform concentration of MC throughout the lens. Polymerization of the MC causes the creation of a second polymer matrix in the exposed region. This second polymer matrix causes a change in the optical properties of the lens in the exposed region. The migration of unpolymerized MC causes swelling of the lens in the exposed region. This in turn alters the shape of the element, again changing the optical properties. When the UV source is removed, the unpolymerized MC in the unexposed lens will migrate within the lens to reestablish equilibrium. This in turn can cause a change in the shape of the lens. This change in shape causes further changes in the optical properties of the lens. Whether a change in shape occurs depends, in part, on the flexibility of the lens, which in turn depends in part on the $T_g$ of the polymer used to form the first polymer matrix or due to the plasticization of the FPM by a medium or a plasticizer or MC. If the polymer has a low $T_g$, then the lens will be flexible and a more pronounced shape change will occur. If the polymer has a high $T_g$, then the lens will be less flexible and less shape change will occur. When no shape change occurs, the change in optical properties will occur strictly based on the change in refractive index caused by the localized polymerization of the MC. The changes occur in specific regions within the lens allowing for the creation of customized lenses, including multifocal lenses.

In a preferred embodiment, the MC with a photopolymerizable group is associated with a polymerization initiator which responds to ultraviolet light. In this case, the lens blank is exposed to ultraviolet light in a pattern to achieve the desired changes in optical properties of the lens.

The lenses of the invention are preferably formed by forming the first polymer matrix in a predetermined form in the presence of the MC. In this embodiment, the starting materials for the first polymer matrix and the MC as well as any necessary adjuvants and catalysts or initiators are combined in a mold in the shape of the desired lens or element. The first polymer matrix is then formed by polymerizing the starting materials. As discussed above, the mechanism used to polymerize the starting material must be such that it does not cause significant polymerization of the MC. While some polymerization of the MC may occur, it should not deplete the amount of free MC in the lens to a level where no change of optical properties can be accomplished through the polymerization of the remaining MC. For this reason, the mechanism used to polymerized the starting materials for the first polymer matrix should be different that that used to polymerize the MC or the polymerization rate for the starting materials should be significantly greater for the starting materials than for the MC.

Polymerization of the starting materials continues until the supply of starting materials is exhausted or the first polymer matrix is such that it forms a self-contained, self supporting structure. By forming the matrix in the presence of the MC, the MC becomes dispersed within the matrix. The lens is then removed from the mold and is ready for further customization. This is accomplished by exposing the lens to external stimuli as described above.

The following is an example of a method that can be used to form the adjustable lenses useful in the practice of the invention. Silicone based first polymer matrix starting materials comprising a vinyl endcapped silicone macromers and hydroxyl endcapped organosilicon compounds are combined in a mold with a silicone based MC such as those described above. A photoinitiator and a catalyst are also added to the composition as well as any required adjuvants such as UV absorbers and the like. Upon addition of the catalyst, the silicone based starting materials polymerize to form the first polymer matrix leaving the MC, photoinitiator and other components unaffected and dispersed within the matrix. The MC can then be exposed to a suitable light source and polymerized causing he desired change in optical properties.

In an alternative embodiment, an aqueous solution of high molecular weight (>10,000) derivatized PVA (dPVA) with reactive methacrylate side groups and low molecular weight (~1,000) dPVA with reactive acrylate side groups and a photoinitiator is place in a mold. The low molecular weight dPVA is the MC in this embodiment. The solution is than exposed to ultraviolet light such that the high molecular weight dPVA polymerizes to form the first polymer matrix. While some of the low molecular weight dPVA may also polymerize, a significant portion remains unpolymerized when the matrix is formed along with some of the free methacrylate groups on the high DPVA may remain free. This unpolymerized low molecular weight dPVA is the free to be polymerized at a later time, thereby causing changes in the optical properties of the lens. In a similar manner, PHEMA abased system can be used where the high molecular weight component has reactive methacrylate groups and the low molecular weight components contain acrylate based groups.

The methods for forming the lenses are illustrative of the techniques that may be used in the practice of the invention. Other methods for forming lenses useful in the practice of the invention are know to those skilled in the art.

The method of the invention can be used to dispense ophthalmic lenses which include corrective spectacles and contact lenses. In this embodiment, the user of the lens is first examined to determine the optical requirements for the lenses. This is done through standard ophthalmologic examination methods such as visual acuity testing, and the like.

Once the optical requirements of the lens are determined, a lens is selected and then exposed to an external stimulus in a pattern and at an intensity so as to produce the desired changes in optical properties. For example, for a patient with hyperopia, the central portion of the lens is exposed to the stimulus or a profiled beam that causes polymerization to occur at a desired depth wise and site specific. In the case of myopia, the outer edges of the lens are exposed or a profiled beam that causes polymerization to occur at a desired depth wise and site specific. Presbyopia can be corrected by exposing the lens in a pattern of concentric rings, thereby creating a multifocal lens. Astigmatism can also be corrected through the use of the appropriate pattern along a certain meridian.

In one embodiment, the customization of the lenses is accomplished at a central facility or distribution point. In this embodiment, the lens requirements are transmitted to the distribution point, a set of lenses is selected, and each lens is separately exposed to an external stimulus to produce the desired changes in optical properties and the distribution facility then sends the customized lenses to the dispensing location.

In an alternative embodiment, the lenses are customized at the dispensing location. In this instance, once the desired lens properties have been determined, a lens is then modified in the manner described above to create a customized lens that meets the requirements of the patient. This second embodiment allows for more precise customization of the lens. In the case of corrective lenses or contact lenses, it is possible to prepare a customized lens, allow the patient to wear the lens, evaluate the vision correction with the lens and, if necessary, further change the optical properties to optimize the correction of the lenses.

EXAMPLE 1

Materials comprising various amounts of (a) poly-dimethylsiloxane endcapped with 10 diacetoxymethylsilane ("PDMS") (36000 g/mol), (b) dimethylsiloxane-diphenylsiloxane copolymer endcapped with vinyl-dimethyl silane ("DMDPS") (15,500 g/mol), and (c) a UV-photoinitiator, 2,2-dimethoxy-2-phenylacetophenone ("DMPA") as shown by Table 1 were made and tested. PDMS is the monomer which forms first polymer matrix, and DMDPS and DMPA together comprise the refraction modulating composition.

TABLE 1

| | PDMS (wt. %) | DMDPS (wt. %) | DMPA (wt. %)a |
|---|---|---|---|
| 1 | 90 | 10 | 1.5 |
| 2 | 80 | 20 | 1.5 |
| 3 | 75 | 25 | 1.5 |
| 4 | 70 | 30 | 1.5 |

WT % WITH RESPECT TO DMDPS.

Briefly, appropriate amounts of PMDS (Gelest DMS-D33; 36000 g/mol), DMDPS (Gelest PDV-0325; 3.0–3.5 mole % diphenyl, 15,500 g/mol), and DMPA (Acros; 1.5 wt % with respect to DMDPS) were weighed together in an aluminum pan, manually mixed at room temperature until the DMPA dissolved, and degassed under pressure (5 mtorr) for 2–4 minutes to remove air bubbles. Photosensitive prisms were fabricated by pouring the resulting silicone composition into a mold made of three glass slides held together by scotch tape in the form of a prism and sealed at one end with silicone caulk. The prisms are ~5 cm long and the dimensions of the three sides are ~8 mm each. The PDMS in the prisms was moisture cured and stored in the dark at room temperature for a period of 7 days to ensure that the resulting first polymer matrix was non-tacky, clear, and transparent.

The amount of photo initiator (1.5 wt. %) was based on prior experiments with fixed MC monomer content of 25% in which the photoinitiator content was varied. Maximal refractive index modulation was observed for compositions containing 1.5% and 2 wt. % photoinitiator while saturation in refractive index occurred at 5 wt. %.

EXAMPLE 2

Synthesis MC Monomers

As illustrated by Scheme 1, commercially available cyclic dimethylsiloxane tetramer ("D$_4$"), cyclic methylphenylsiloxane trimer ("D$_3$'") in various ratios were ring-opened by triflic acid and bis-methacryloxylpropyltetramethyldisiloxane ("MPS") were reacted in a one pot synthesis. U.S. Pat. No. 4,260,725; Kunzler, J. F., Trends in Polymer Science, 4: 52–59 (1996); Kunzler et al. J. Appl. Poly. Sci., 55: 611–619 (1995); and Lai et al., J. Poly. Sci. A. Poly. Chem., 33:1773–1782 (1995).

SCHEME 1

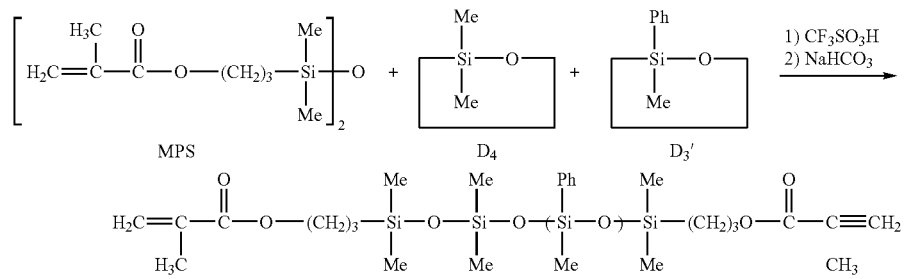

RMC Monomer

Briefly, appropriate amounts of MPS, D$_4$, and D$_3$' were stirred in a vial for 1.5–2 hours. An appropriate amount of triflic acid was added and the resulting mixture was stirred for another 20 hours at room temperature. The reaction mixture was diluted with hexane, neutralized (the acid) by the addition of sodium bicarbonate, and dried by the addition of anhydrous sodium sulfate. After filtration and rotovaporation of hexane, the MC monomer was purified by further filtration through an activated carbon column. The MC monomer was dried at 5 mtorr of pressure between 70–80° C. for 12–18 hours.

The amounts of phenyl, methyl, and endgroup incorporation were calculated from $^1$H-NMR spectra that were run in deuterated chloroform without internal standard tetramethylsilane ("TMS"). Illustrative examples of chemical shifts for some of the synthesized MC monomers follows. A 1000 g/mole MC monomer containing 5.58 mole % phenyl (made by reacting: 4.85 g (12.5 mmole) of MPS; 1.68 g (4.1 mmole) of $D_3'$; 5.98 g (20.2 mmole) of $D_4$; and 110 µl (1.21 mmole) of triflic acid: δ=7.56–7.57 ppm (m, 2H) aromatic, δ=7.32–7.33 ppm (m, 3H) aromatic, δ=6.09 ppm (d, 2H) olefinic, δ=5.53 ppm (d, 2H) olefinic, δ=4.07–4.10 ppm (t, 4H) —O—$CH_2CH_2CH_2$—, δ=1.93 ppm (s, 6H) methyl of methacrylate, δ=1.65–1.71 ppm (m, 4H)—O—$CH_2CH_2CH_2$—, δ=0.54–0.58 ppm (m, 4H) —O—$CH_2CH_2CH_2$—Si, δ=0.29–0.30 ppm (d, 3H), $CH_3$—Si-Phenyl, δ 0.04–0.08 ppm (s, 50 H) $(CH_3)_2Si$ of the backbone.

A 2000 g/mole MC monomer containing 5.26 mole % phenyl (made by reacting: 2.32 g (6.0 mmole) of MPS; 1.94 g (4.7 mmole) of $D_3'$; 7.74 g (26.1 mmole) of $D_4$ and 140 µl (1.54 mmole) of triflic acid: δ=7.54–7.58 ppm (m, 4H) aromatic, δ=7.32–7.34 ppm (m, 6H) aromatic, δ=6.09 ppm (d, 2H) olefinic, δ=5.53 ppm (d, 2H) olefinic, δ=4.08–4.11 ppm (t, 4H) —O—$CH_2CH_2CH_2$—, δ=1.94 ppm (s, 6H) methyl of methacrylate, δ=1.67–1.71 ppm (m, 4H) —O—$CH_2CH_2CH_2$—, δ=0.54–0.59 ppm (m, 4H) —O—$CH_2CH_2CH_2$—Si, δ=0.29–0.31 ppm (m, 6H), $CH_3$—Si-Phenyl, δ=0.04–0.09 ppm (s, 112H) $(CH_3)_2Si$ of the backbone.

A 4000 g/mole MC monomer containing 4.16 mole % phenyl (made by reacting: 1.06 g (2.74 mmole) of MPS; 1.67 g (4.1 mmole) of $D_3'$; 9.28 g (31.3 mmole) of $D_4$ and 160 µl (1.77 mmole) of triflic acid: δ=7.57–7.60 ppm (m, 8H) aromatic, δ=7.32–7.34 ppm (m,12H) aromatic, δ=6.10 ppm (d, 2H) olefinic, δ=5.54 ppm (d, 2H) olefinic, δ=4.08–4.12 ppm (t, 4H) —O—$CH_2CH_2CH_2$—, δ=1.94 ppm (s, 6H) methyl of methacrylate, δ=1.65–1.74 ppm (m, 4H) —O—$CH_2CH_2CH_2$—, δ=0.55–0.59 ppm (m, 4H) —O—$CH_2CH_2CH_2$—Si, δ=0.31 ppm (m, 11H), $CH_3$—Si-Phenyl, δ=0.07–0.09 ppm (s, 272 H) $(CH_3)_2Si$ of the backbone.

Similarly, to synthesize dimethylsiloxane polymer without any methylphenylsiloxane units and endcapped with methyacryloxypropyl dimethylsilane, the ratio of $D_4$ to MPS was varied without incorporating $D'_3$.

Molecular weights were calculated by $^1$H-NMR and by gel permeation chromatography ("GPC"). Absolute molecular weights were obtained by universal calibration method using polystyrene and poly(methyl methacrylate) standards. Table 2 shows the characterization of other MC monomers synthesized by the triflic acid ring opening polymerization.

TABLE 2

|   | Mole % Phenyl | Mole % Methyl | Mole % Methacrylate | Mn (NMR) | Mn (GPC) |   |
|---|---|---|---|---|---|---|
| A | 6.17 | 87.5 | 6.32 | 1001 | 946 | 1.44061 |
| B | 3.04 | 90.8 | 6.16 | 985 | 716 | 1.43188 |
| C | 5.26 | 92.1 | 2.62 | 1906 | 1880 | — |
| D | 4.16 | 94.8 | 1.06 | 4054 | 4200 | 1.42427 |
| E | 0 | 94.17 | 5.83 | 987 | 1020 | 1.42272 |
| F | 0 | 98.88 | 1.12 | 3661 | 4300 | 1.40843 |

At 10–40 wt %, these MC monomers of molecular weights 1000 to 4000 g/mol with 3–6.2 mole % phenyl content are completely miscible, biocompatible, and form optically clear prisms and lenses when incorporated in the silicone matrix. MC monomers with high phenyl content (4–6 mole %) and low molecular weight (1000–4000 g/mol) resulted in increases in refractive index change of 2.5 times and increases in speeds of diffusion of 3.5 to 5.0 times compared to the MC monomer used in Table 1 (dimethylsiloxane-diphenylsiloxane copolymer endcapped with vinyldimethyl silane ("DMDPS") (3–3.5 mole % diphenyl content, 15500 g/mol). These MC monomers were used to make optical elements comprising: (a) poly-dimethylsiloxane endcapped with diacetoxymethylsilane ("PDMS") (36000 g/mol), (b) dimethylsiloxane methylphenylsiloxane copolymer that is endcapped with a methacryloxylpropyldimethylsilane group, and (c) 2,2-dimethoxy-2-phenylacetophenone ("DMPA"). Note that component (a) is the monomer that forms the first polymer matrix and components (b) and (c) comprise the refraction modulating composition.

EXAMPLE 3

Fabrication of Intraocular Lenses ("IOL")

An intraocular mold was designed according to well-accepted standards. See e.g., U.S. Pat. Nos. 5,762,836; 5,141,678; and 5,213,825. Briefly, the mold is built around two plano-concave surfaces possessing radii of curvatures of −6.46 mm and/or −12.92 mm, respectively. The resulting lenses are 6.35 mm in diameter and possess a thickness ranging from 0.64 mm, 0.98 mm, or 1.32 mm depending upon the combination of concave lens surfaces used. Using two different radii of curvatures in their three possible combinations and assuming a nominal refractive index of 1.404 for the IOL composition, lenses with pre-irradiation powers of 10.51 D (62.09 D in air), 15.75 D (92.44 in air), and 20.95 D (121.46 D in air) were fabricated.

FUTURE EXAMPLE 3A (CONTACT LENS)

EXAMPLE 4

Stability of Compositions Against Leaching

Three IOLs were fabricated with 30 and 10 wt % of MC monomers B and D incorporated in 60 wt % of the PDMS matrix. After moisture curing of PDMS to form the first polymer matrix, the presence of any free MC monomer in the aqueous solution was analyzed as follows. Two out of three lenses were irradiated three times for a period of 2 minutes using 340 nm light, while the third was not irradiated at all. One of the irradiated lenses was then locked by exposing the entire lens matrix to radiation. All three lenses were mechanically shaken for 3 days in 1.0 M NaCl solution. The NaCl solutions were then extracted by hexane and analyzed by $^1$H-NMR. No peaks due to the MC monomer were observed in the NMR spectrum. These results suggest that the MC monomers did not leach out of the matrix into the aqueous phase in all three cases. Earlier studies on a vinyl endcapped silicone MC monomer showed similar results even after being stored in 1.0 M NaCl solution for more than one year.

EXAMPLE 5

Toxicological Studies in Rabbit Eyes

Sterilized, unirradiated and irradiated silicone IOLs (fabricated as described in Example 3) of the present invention and a sterilized commercially available silicone IOL were implanted in albino rabbit eyes. After clinically following the eyes for one week, the rabbits were sacrificed. The extracted eyes were enucleated, placed in formalin and studied histopathologically. There is no evidence of corneal toxicity, anterior segment inflammation, or other signs of lens toxicity.

EXAMPLE 6

Irradiation of Silicone Prisms

Because of the ease of measuring refractive index change (n) and percent net refractive index change (% n) of prisms, the inventive formulations were molded into prisms for irradiation and characterization. Prisms were fabricated by mixing and pouring (a) 90–60 wt % of high Mn PDMS, (b) 10–40 wt % of MC monomers in Table 2, and (c) 0.75 wt % (with respect to the MC monomers) of the photoinitiator DMPA into glass molds in the form of prisms 5 cm long and 8.0 mm on each side. The silicone composition in the prisms was moisture cured and stored in the dark at room temperature for a period of 7 days to ensure that the final matrix was non-tacky, clear and transparent.

Two of the long sides of each prism were covered by a black background while the third was covered by a photomask made of an aluminum plate with rectangular windows (2.5 mm×10 mm). Each prism was exposed to a flux of 3.4 mW/cm$^2$ of a collimated 340 nm light (peak absorption of the photoinitiator) from a 1000 W Xe:Hg arc lamp for various time periods. The ANSI guidelines indicate that the maximum permissible exposure ("MPE") at the retina using 340 nm light for a 10–30000 s exposure is 1000 mJ/cm$^2$. Criteria for Exposure of Eye and Skin. *American National Standard* Z136.1: 31–42 (1993). The single dose intensity 3.4 mW/cm$^2$ of 340 nm light for a period of 2 minutes corresponds to 408 mJ/cm$^2$ which is well within the ANSI guidelines. FIG. 2 is an illustration of the prism irradiation procedure.

The prisms were subject to both (i) continuous irradiation—one-time exposure for a known time period, and (ii) "staccato" irradiation—three shorter exposures with long intervals between them. During continuous irradiation, the refractive index contrast is dependent on the cross-linking density and the mole % phenyl groups, while in the interrupted irradiation, MC monomer diffusion and further cross-linking also play an important role. During staccato irradiation, the MC monomer polymerization depends on the rate of propagation during each exposure and the extent of interdiffusion of free MC monomer during the intervals between exposures. Typical values for the diffusion coefficient of oligomers (similar to the 1000 g/mole MC monomers used in the practice of the present invention) in a silicone matrix are on the order of $10^{-6}$ to $10^{-7}$ cm$^2$/s. In other words, the inventive MC monomers require approximately 2.8 to 28 hours to diffuse 1 mm (roughly the half width of the irradiated bands). The distance of a typical optical zone in an IOL is about 4 to about 5 mm across. However, the distance of the optical zone may also be outside of this range. After the appropriate exposures, the prisms were irradiated without the photomask (thus exposing the entire matrix) for 6 minutes using a medium pressure mercury-arc lamp. This polymerized the remaining silicone MC monomers and thus "locked" the refractive index of the prism in place. Notably, the combined total irradiation of the localized exposures and the "lock-in" exposure was still within ANSI guidelines.

EXAMPLE 7

Prism Dose Response Curves

Inventive prisms fabricated from MC monomers described by Table 2 were masked and initially exposed for 0.5, 1, 2, 5, and 10 minutes using 3.4 mW/cm$^2$ of the 340 nm line from a 1000 W Xe:Hg arc lamp. The exposed regions of the prisms were marked, the mask detached and the refractive index changes measured. The refractive index modulation of the prisms was measured by observing the deflection of a sheet of laser light passed through the prism. The difference in deflection of the beam passing through the exposed and unexposed regions was used to quantify the refractive index change ($\Delta n$) and the percentage change in the refractive index (% $\Delta n$).

After three hours, the prisms were remasked with the windows overlapping with the previously exposed regions and irradiated for a second time for 0.5, 1, 2, and 5 minutes (total time thus equaled 1, 2, 4, and 10 minutes respectively). The masks were detached and the refractive index changes measured. After another three hours, the prisms were exposed a third time for 0.5, 1, and 2 minutes (total time thus equaled 1.5, 3, and 6 minutes) and the refractive index changes were measured. As expected, the % $\Delta n$ increased with exposure time for each prism after each exposure resulting in prototypical dose response curves, Based upon these results, adequate MC monomer diffusion appears to occur in about 3 hours for 1000 g/mole MC monomer.

All of the MC monomers (B–F) except for MC monomer A resulted in optically clear and transparent prisms before and after their respective exposures. For example, the largest % n for MC monomers B, C, and D at 40 wt % incorporation into 60 wt % FPMC were 0.52%, 0.63% and 0.30% respectively which corresponded to 6 minutes of total exposure (three exposures of 2 minutes each separated by 3 hour intervals for MC monomer B and 3 days for MC monomers C and D). However, although it produced the largest change in refractive index (0.95%), the prism fabricated from MC monomer A (also at 40 wt % incorporation into 60 wt % FPMC and 6 minutes of total exposure—three exposures of 2 minutes each separated by 3 hour intervals) turned somewhat cloudy. Thus, if MC monomer A were used to fabricate an IOL, then the MC must include less than 40 wt % of MC monomer A or the % $\Delta n$ must be kept below the point where the optical clarity of the material is compromised.

A comparison between the continuous and staccato irradiation for MC A and C in the prisms shows that lower % $\Delta n$ values occurs in prisms exposed to continuous irradiation as compared to those observed using staccato irradiations. As indicated by these results, the time interval between exposures (which is related to the amount of MC diffusion from the unexposed to exposed regions) may be exploited to precisely modulate the refractive index of any material made from the inventive polymer compositions.

Exposure of the entire, previously irradiated prisms to a medium pressure Hg arc lamp polymerized any remaining free MC. effectively locking the refractive index contrast. Measurement of the refractive index change before and after photolocking indicated no further modulation in the refractive index.

EXAMPLE 8

Optical Characterization of IOLs

Talbot interferometry and the Ronchi test were used to qualitatively and quantitatively measure any primary optical aberrations (primary spherical, coma, astigmatism, field curvature, and distortion) present in pre- and post-irradiated lenses as well as quantifying changes in power upon photopolymerization.

In Talbot interferometry, the test IOL is positioned between the two Ronchi rulings with the second grating placed outside the focus of the IOL and rotated at a known angle θ, with respect to the first grating.

Superposition of the autoimage of the first Ronchi ruling ($p_1$=300 lines/inch) onto the second grating ($P_2$=150 lines/inch) produces moire fringes inclined at an angle, $\alpha_1$. A second moire fringe pattern is constructed by axial displacement of the second Ronchi ruling along the optic axis a known distance, d, from the test lens. Displacement of the second grating allows the autoimage of the first Ronchi ruling to increase in magnification causing the observed moire fringe pattern to rotate to a new angle, $\alpha_2$. Knowledge of moiré pitch angles permits determination of the focal length of the lens (or inversely its power) through the expression:

$$f = \frac{p_1}{p_2} d \left( \frac{1}{\tan\alpha_2 \sin\theta + \cos\theta} - \frac{1}{\tan\alpha_1 \sin\theta + \cos\theta} \right)^{-1}$$

To illustrate the applicability of Talbot interferometry to this work, moire fringe patterns of one of the inventive, pre-irradiated IOLs (60 wt % PDMS, 30 wt % MC monomer B, 10 wt % MC monomer D, and 0.75% DMPA relative to the two MC monomers) measured in air is presented in FIG. 3. Each of the moire fringes was fitted with a least squares fitting algorithm specifically designed for the processing of moire patterns. The angle between the two Ronchi rulings was set at 12°, the displacement between the second Ronchi ruling between the first and second moire fringe patterns was 4.92 mm, and the pitch angles of the moiré fringes, measured relative to an orthogonal coordinate system defined by the optic axis of the instrument and crossing the two Ronchi rulings at 90, were $\alpha_1$=-33.2±0.30 and $\alpha_2$=-52.7±0.40. Substitution of these values into the above equation results in a focal length of 10.71±0.50 mm (power=93.77±4.6 D).

Optical aberrations of the inventive IOLs (from either fabrication or from the stimulus-induced polymerization of the MC components) were monitored using the "Ronchi Test" which involves removing the second Ronchi ruling from the Talbot interferometer and observing the magnified autoimage of the first Ronchi ruling after passage though the test IOL. The aberrations of the test lens manifest themselves by the geometric distortion of the fringe system (produced by the Ronchi ruling) when viewed in the image plane. A knowledge of the distorted image reveals the aberration of the lens. In general, the inventive fabricated lenses (both pre and post irradiation treatments) exhibited sharp, parallel, periodic spacing of the interference fringes indicating an absence of the majority of primary-order optical aberrations, high optical surface quality, homogeneity of n in the bulk, and constant lens power. FIG. 4 is an illustrative example of a Ronchigram of an inventive, pre-irradiated IOL that was fabricated from 60 wt % PDMS, 30 wt % MC monomer B, 10 wt % MC monomer D, and 0.75% of DMPA relative to the 2 MC monomers.

The use of a single Ronchi ruling may also be used to measure the degree of convergence of a refracted wavefront (i.e., the power). In this measurement, the test IOL is placed in contact with the first Ronchi ruling, collimated light is brought incident upon the Ronchi ruling, and the lens and the magnified autoimage is projected onto an observation screen. Magnification of the autoimage enables measurement of the curvature of the refracted wavefront by measuring the spatial frequency of the projected fringe pattern. These statements are quantified by the following equation:

$$P_r = \frac{1000}{L}\left(1 + \frac{d_s}{d}\right)$$

wherein $P_v$ is the power of the lens expressed in diopters, L is the distance from the lens to the observing plane, $d_s$, is the magnified fringe spacing of the first Ronchi ruling, and d is the original grating spacing.

EXAMPLE 9

Power Changes from Photopolymerization of the Inventive IOLs

An inventive IOL was fabricated as described by Example 3 comprising 60 wt % PDMS ($n_D$=1.404), 30 wt % of MC monomer B ($n_D$=1.4319), 10 wt % of MC monomer D ($n_D$=1.4243), and 0.75 wt % of the photoinitiator DMPA relative to the combined weight percents of the two MC monomers. The IOL was fitted with a 1 mm diameter photomask and exposed to 3.4 mW/cm$^2$ of 340 nm collimated light from a 1000 W Xe:Hg arc lamp for two minutes. The irradiated lens was then placed in the dark for three hours to permit polymerization and MC monomer diffusion. The IOL was photolocked by continuously exposing the entire lens for six minutes using the aforementioned light conditions. Measurement of the moiré pitch angles followed by substitution into equation 1 resulted in a power of 95.1±2.9 D (f=10.52±0.32 mm) and 104.1±3.6 D (f=9.61 mm±0.32 mm) for the unirradiated and irradiated zones, respectively.

The magnitude of the power increase was more than what was predicted from the prism experiments where a 0.6% increase in the refractive index was routinely achieved, If a similar increase in the refractive index was achieved in the IOL, then the expected change in the refractive index would be 1.4144 to 1.4229. Using the new refractive index (1.4229) in the calculation of the lens power (in air) and assuming the dimensions of the lens did not change upon photopolymerization, a lens power of 96.71 D (f=10.34 mm) was calculated. Since this value is less than the observed power of 104.1±3.6 D, the additional increase in power must be from another mechanism.

Further study of the photopolymerized IOL showed that subsequent MC monomer diffusion after the initial radiation exposure leads to changes in the radius of curvature of the lens. See e.g., FIG. 5. The MC monomer migration from the unradiated zone into the radiated zone causes either or both of anterior and posterior surfaces of the lens to swell thus changing the radius of curvature of the lens. It has been determined that a 7% decrease in the radius of curvature for both surfaces is sufficient to explain the observed increase in lens power.

The concomitant change in the radius of curvature was further studied. An identical IOL described above was fabricated. A Ronchi interferogram of the IOL is shown in FIG. 6a (left interferogram). Using a Talbot interferometer, the focal length of the lens was experimentally determined to be 10.52±0.30 mm (95.1 D±2.8 D). The IOL was then fitted with a 1 mm photomask and irradiated with 3.4 mW/cm$^2$ of 340 nm collimated light from a 1000 W Xe:Hg arc lamp continuously for 2.5 minutes. Unlike the previous IOL, this lens was not "locked in" three hours after irradiation. FIG. 6b (right interferogram) is the Ronchi interferogram of the lens taken six days after irradiation. The most obvious feature between the two interference patterns is the dramatic increase in the fringe spacing, which is indicative of an increase in the refractive power of the lens.

Measurement of the fringe spacings indicates an increase of approximately +38 diopters in air (f≈7.5 mm). This corresponds to a change in the order of approximately +8.6 diopters in the eye. Since most post-operative corrections from cataract surgery are within 2 diopters, this experiment indicates that the use of the inventive IOLs will permit a relatively large therapeutic window.

EXAMPLE 10

Photopolymerization Studies of Non-Phenyl-Containing IOLs

Inventive IOLs containing non-phenyl containing MC monomers were fabricated to further study the swelling from the formation of the second polymer matrix. An illustrative example of such an IOL was fabricated from 60 wt % PDMS, 30 wt % MC monomer E, 10 wt % MC monomer F, and 0.75% DMPA relative to the two MC monomers. The pre-irradiation focal length of the resulting IOL was 10.76 mm (92.94±2.21 D).

In this experiment, the light source was a 325 nm laser line from a He:Cd laser. A 1 mm diameter photomask was placed over the lens and exposed to a collimated flux of 0.75 mW/cm$^2$ at 325 nm for a period of two minutes. The lens was then placed in the dark for three hours. Experimental measurements indicated that the focal length of the IOL changed from 10.76 mm±0.25 mm (92.94 D±2.21 D) to 8.07 mm±0.74 mm (123.92 D±10.59 D) or a dioptric change of +30.98 D±10.82 D in air. This corresponds to an approximate change of +6.68 D in the eye. The amount of irradiation required to induce these changes is only 0.09 J/cm$^2$, a value well under the ANSI maximum permissible exposure ("MPE") level of 1.0 J/cm$^2$.

EXAMPLE 11

Monitoring for Potential IOL Changes from Ambient Light

The optical power and quality of the inventive IOLs were monitored to show that handling and ambient light conditions do not produce any unwanted changes in lens power. A 1 mm open diameter photomask was placed over the central region of an inventive IOL (containing 60 wt % PDMS, 30 wt % MC monomer E, 10 wt % MC monomer F, and 0.75 wt % DMPA relative to the two MC monomers), exposed to continuous room light for a period of 96 hours, and the spatial frequency of the Ronchi patterns as well as the moiré fringe angles were monitored every 24 hours. Using the method of moiré fringes, the focal length measured in the air of the lens immediately after removal from the lens mold is 10.87±0.23 mm (92.00 D±1.98 D) and after 96 hours of exposure to ambient room light is 10.74 mm±0.25 mm (93.11 D±2.22 D). Thus, within the experimental uncertainty of the measurement, it is shown that ambient light does not induce any unwanted change in power. A comparison of the resulting Ronchi patterns showed no change in spatial frequency or quality of the interference pattern, confirming that exposure to room light does not affect the power or quality of the inventive IOLs.

EXAMPLE 12

Effect of the Lock in Procedure of an Irradiated IOL

An inventive IOL whose power had been modulated by irradiation was tested to see if the lock-in procedure resulted in further modification of lens power. An IOL fabricated from 60 wt % PDMS, 30 wt % MC monomer E, 10 wt % MC monomer F, and 0.75% DMPA relative to the two MC monomers was irradiated for two minutes with 0.75 mW/cm$^2$ of the 325 nm laser line from a He:Cd laser and was exposed for eight minutes to a medium pressure Hg arc lamp. Comparisons of the Talbot images before and after the lock in procedure showed that the lens power remained unchanged. The sharp contrast of the interference fringes indicated that the optical quality of the inventive lens also remained unaffected.

To determine if the lock-procedure was complete, the IOL was refitted with a 1 mm diameter photomask and exposed a second time to 0.75 mW/cm$^2$ of the 325 laser line for two minutes. As before, no observable change in fringe space or in optical quality of the lens was observed.

EXAMPLE 13

Monitoring for Potential IOL Changes from the Lock-in

A situation may arise wherein the implanted IOL does not require post-operative power modification. in such cases, the IOL must be locked in so that its characteristic will not be subject to change. To determine if the lock-in procedure induces undesired changes in the refractive power of a previously unirradiated IOL, the inventive IOL (containing 60 wt % PDMS, 30 wt % MC monomer E, 10 wt % MC monomer F, and 0.75 wt % DMPA relative to the two MC monomers) was subject to three 2 minute irradiations over its entire area that was separated by a 3 hour interval using 0.75 mW/cm$^2$ of the 325 laser line from a He:Cd laser. Ronchigrams and moire fringe patterns were taken prior to and after each subsequent irradiation. The moire fringe patterns taken of the inventive IOL in air immediately after removal from the lens mold and after the third 2 minute irradiation indicate a focal length of 10.50 mm±0.39 mm (95.24 D±3.69 D) and 10.12 mm±0.39 mm (93.28 D±3.53D) respectively. These measurements indicate that photolocking a previously unexposed lens does not induce unwanted changes in power. In addition, no discernable change in fringe spacing or quality of the Ronchi fringes was detected indicating that the refractive power had not changed due to the lock-in.

In a third embodiment, the lenses are manufactured at a central facility and the initial customization is done at that location. The lens is then sent to the dispensing location. The lens may be further modified at the dispensing location based on feedback from the patient after use of the lens.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for customizing a lens post fabrication comprising:
   a) conducting an examination of a patient to determine the optical properties required for the lens;
   b) selecting a lens, said lens capable of post manufacture modification by exposure to an external energy source;
   c) exposing at least a portion of the lens to induce changes in the optical properties of the lens to match the optical properties required for the lens;
   d) exposing the entire lens to an external energy source to lock in the induced changes in the optical properties of the lens;
   e) dispensing the lens to the patient.

2. The method of claim 1 wherein said lens comprises a modifying composition dispersed within the lens, the modifying composition capable of stimulus induced polymerization.

3. The method of claim 1 further comprising the step of re-exposing at least a portion of the lens to an external energy source at least once to induce further changes in the optical properties of the lens.

4. The method of claim 1 wherein the modifying composition comprises at least one photopolymerizable moiety.

5. The method of claim 1 wherein the external energy source is light.

6. The method of claim 1 wherein the external energy source is ultraviolet light.

7. The method of claim 1 wherein the lens is a corrective lens for glasses.

8. The method of claim 1 wherein the lens is a contact lens.

9. The method of claim 1 wherein the lens comprises a first polymer matrix.

10. The method of claim 7 wherein the modifying composition comprises at least one photopolymerizable moiety.

11. The method of claim 7 wherein the external energy source is light.

12. The method of claim 7 wherein the external energy source is ultraviolet light.

13. A method for customizing a lens comprising the steps of:
   a) determining the optical requirements of the lens;
   b) selecting a lens, said lens comprising a modifying composition;
   c) exposing at least a portion of the lens to an external energy source, thereby inducing changes in the optical properties of the lens;
   d) measuring the optical properties of the lens;
   e) re-exposing at least a portion of the lens to an external energy source inducing further changes in the optical properties of the lens;
   f) repeating steps (d) and (e) until the measured optical properties of the lens match the optical requirements of the lens;
   g) exposing the entire lens to an external energy source to lock-in the previous changes in the optical properties.

14. The method of claim 13 wherein the step of determining the optical requirements of the lens is accomplished by conducting an ophthalmologic examination of a patient.

15. The method of claim 13 wherein the lens is a corrective lens for glasses.

16. The method of claim 13 wherein the lens is a contact lens.

* * * * *